(12) United States Patent
Baldenius et al.

(10) Patent No.: US 7,824,891 B2
(45) Date of Patent: *Nov. 2, 2010

(54) METHOD FOR PRODUCING D-PANTOTHENIC ACID AND/OR SALTS THEREOF VIA PURIFICATION BY ELECTRODIALYSIS AS AN ADDITIVE FOR ANIMAL FEED

(75) Inventors: Kai-Uwe Baldenius, Ludwigshafen (DE); Christine Beck, Mannheim (FR); Andreas Fischer, Ludwigshafen (DE); Hans-Peter Harz, Dudenhofen (DE); Markus Lohscheidt, Mannheim (DE); Martin Leemann, Bensheim (DE)

(73) Assignee: Basf SE, Ludwigshafen (DE)

( * ) Notice: Subject to any disclaimer, the term of this patent is extended or adjusted under 35 U.S.C. 154(b) by 581 days.

This patent is subject to a terminal disclaimer.

(21) Appl. No.: 10/468,610

(22) PCT Filed: Feb. 20, 2002

(86) PCT No.: PCT/EP02/01766

§ 371 (c)(1),
(2), (4) Date: Aug. 21, 2003

(87) PCT Pub. No.: WO02/066666

PCT Pub. Date: Aug. 29, 2002

(65) Prior Publication Data

US 2004/0072306 A1    Apr. 15, 2004

(30) Foreign Application Priority Data

Feb. 21, 2001   (DE) ............................... 101 08 223

(51) Int. Cl.
*C12P 13/04*   (2006.01)
*C12P 21/02*   (2006.01)
*C07G 13/00*   (2006.01)
*C07C 229/08*  (2006.01)

(52) U.S. Cl. ...................... 435/106; 435/69.1; 426/239; 204/157.67; 562/569

(58) Field of Classification Search ................ 435/106, 435/116, 69.1, 244; 426/239; 204/157.67; 562/569
See application file for complete search history.

(56) References Cited

U.S. PATENT DOCUMENTS

| 5,518,906 A  | * | 5/1996 | Hikichi et al. ............. 435/116 |
| 5,952,206 A  |   | 9/1999 | Giselbrecht et al. |
| 6,110,342 A  | * | 8/2000 | Mani ......................... 204/527 |
| 6,184,007 B1 | * | 2/2001 | Dusch et al. ................ 435/128 |
| 6,280,985 B1 | * | 8/2001 | Caboche et al. ............ 435/139 |
| 6,582,939 B1 | * | 6/2003 | Binder et al. ............... 435/106 |
| 2005/0089973 A1 | * | 4/2005 | Yocum et al. ............... 435/106 |
| 2007/0202571 A1 |   | 8/2007 | Eikmanns et al. |

FOREIGN PATENT DOCUMENTS

| EP | 493 060    |   | 7/1992 |
| EP | 590 857    |   | 6/1994 |
| EP | 1 006192   |   | 6/2000 |
| EP | 1006192 A2 | * | 6/2000 |
| EP | 1 050219   |   | 11/2000 |
| GB | 562 267    |   | 6/1944 |
| WO | 01/21772   |   | 3/2001 |
| WO | 02/24001   |   | 3/2002 |
| WO | 02/057474 A2 |   | 7/2002 |
| WO | 02/061108 A2 |   | 8/2002 |

OTHER PUBLICATIONS

Baigori et al., "Isolation and characterization of *B. subtilis* mutants blocked in the synthesis of pantothenic acid," J Bacteriology 173(13):4240-4242, 1991.*
Lafontaine et al., "Electrodialysis- Turning Seawater into Drinking Water,", online presentation by the Dept. of Chemical Engineering, University of Waterloo, Ontario, Canada, http://cape.uwaterloo.ca/che100projects/sea/ed.html, printed on Jul. 22, 2005.*
Batchelder, "Electrodialysis Applications in Whey Processing," Ionics Technical Paper, Ionics, Inc., Watertown, MA, paper presented at the 1986 International Whey Conference, Oct. 28, 1986, Chicago, IL.*
XP-001002216, Baigori et al. Isolation and Characteri-zation of *Bacillus subtilis*. . . 4240-4242.
XP-002171539.
XP-008004305, Begley et al., The Biosynthesis of Coenzyme A in Bacteria, 157-171.

* cited by examiner

*Primary Examiner*—Karen Cochrane Carlson
*Assistant Examiner*—Rosanne Kosson
(74) *Attorney, Agent, or Firm*—Novak Druce + Quigg LLP

(57) ABSTRACT

The invention relates to an improved method for producing D-pantothenic acid and/or salts thereof and to the use thereof as an additive for animal feed.

20 Claims, No Drawings

METHOD FOR PRODUCING D-PANTOTHENIC ACID AND/OR SALTS THEREOF VIA PURIFICATION BY ELECTRODIALYSIS AS AN ADDITIVE FOR ANIMAL FEED

CROSS-REFERENCE TO RELATED APPLICATIONS

This application is the U.S. national phase of International Application No. PCT/EP02/01766, filed on Feb. 20, 2002, which claims priority to German Application No. DE 10108223.1, filed on Feb. 21, 2001.

NAMES OF PARTIES TO A JOINT RESEARCH AGREEMENT

Subject matter described and claimed in the instant patent was developed pursuant to a joint research agreement between OmniGene Bioproducts, Inc. and BASF Aktiengesellschaft.

The present invention relates to an improved process for preparing D-pantothenic acid and/or salts thereof and to the use thereof as additive to animal feedstuffs.

BACKGROUND OF THE INVENTION

As a starting material of the biosynthesis of coenzyme A, D-pantothenate is widely distributed in the plant and animal kingdoms. In contrast to humans who consume sufficient quantities of pantothenic acid via the diet, symptoms of D-pantothenate deficiency are frequently described not only for plants but also for animals. The availability of D-pantothenate is therefore of great economic interest, particularly in the animal feed industry.

Conventionally, D-pantothenate is prepared by chemical synthesis from D-pantolactone and calcium β-alaninate (Ullmann's Encyclopedia of Industrial Chemistry, $6^{th}$ edition, 1999, electronic release, chapter "Vitamins"). The preparation of D-pantolactone requires complex, classical racemate cleavage via diastereomeric salts. The commercial product resulting from the chemical synthesis is usually the calcium salt of D-pantothenic acid, calcium D-pantothenate.

Compared with chemical synthesis, the advantage of biotechnological production processes using microorganisms is the selective (enantiomerically pure) production of the D form of pantothenic acid, which can be used for higher organisms. A complex racemate cleavage, as required in chemical synthesis, is thus not necessary.

Numerous fermentation processes for preparing D-pantothenic acid using microorganisms are known, including in EP-0 590 857, WO 96/33283, U.S. Pat. No. 6,013,492, WO 97/10340, DE 198 46 499, EP 1 001 027, EP 1 006 189, EP 1 006 192 and EP 1 006 193.

Thus EP 1 006 189 and EP 1 001 027 describe processes for preparing pantothenate in which a content of at most 1 g/l of D-pantothenic acid in the fermentation solution is achieved. Such low pantothenic acid contents in the fermentation solution, that is to say of less than 10% by weight, based on the solids content, are unsuitable, however, for economic preparation of D-pantothenic acid-containing animal feed supplements. A further disadvantage with the processes described to date is that isolating the product from the fermentation medium requires numerous complex work-up steps. An economic preparation process on the industrial scale is not known.

German Laid Open Application DE 100 16 321 describes a fermentation process for preparing a D-pantothenic acid-containing animal feed supplement. However, an important disadvantage of this process, as with the above-described fermentation processes for preparing D-pantothenic acid, is that the pantothenic acid precursor β-alanine must be supplied to the microorganism via the fermentation medium in order to obtain economic yields of the desired product.

In addition, U.S. Pat. No. 6,013,492 and WO 96/332839 describe working up the D-pantothenic acid from the fermentation solution by filtering off insoluble constituents (for example cell material) from the culture medium, adsorbing the filtrate to activated carbon, subsequently eluting the D-pantothenic acid with an organic solvent, preferably methanol, neutralizing with calcium hydroxide and subsequently crystallizing calcium D-pantothenate. Important disadvantages are the losses of valuable product occurring during crystallization and the use of an organic solvent which can only be removed with difficulty from the product and requires a complex solvent recovery step.

EP 0 590 857 describes a fermentation process for preparing D-pantothenic acid in which culturing a microorganism requires the feeding of β-alanine. The fermentation solution is filtered to separate off the biomass, then passed through a cation exchanger and then an anion exchanger, following this neutralizing with calcium hydroxide, concentrating by evaporation, adding activated carbon, filtering once more and crystallizing with addition of methanol and calcium chloride. The resultant calcium pantothenate-containing product, in addition to D-pantothenic acid in the form of the calcium salt, also contains calcium chloride in a molar ratio of 1:1. Decreasing the calcium chloride content requires electrodialysis with subsequent spray drying. This process has the disadvantage of being neither economical or ecological because of the multiplicity of complex process steps and the use of organic solvents.

SUMMARY OF THE INVENTION

It is an object of the present invention to provide an animal feed supplement containing D-pantothenic acid and/or salts thereof and its preparation by an improved process for preparing D-pantothenic acid and/or salts thereof which does not have the above-mentioned disadvantages. For economic reasons, a process is desirable here in which supplying β-alanine is greatly decreased or is not required at all. In addition, preparing D-pantothenic acid in the form of its divalent salts and, especially, the alkaline earth metal salts, is desirable, since the divalent salts have less hygroscopic characteristics than monovalent salts of pantothenic acid and thus have a less pronounced trend to aggregation for further application, for example as animal feed supplement.

We have found that this object is achieved advantageously by the present invention.

The present invention relates to a process for preparing D-pantothenic acid and/or salts thereof which comprises a) using at least one organism which produces D-pantothenic acid and in which the biosynthesis of pantothenic acid (pan) and/or isoleucine/valine (ilv) is deregulated and which forms at least 2 g/l of salts of D-pantothenic acid by fermentation in a culture medium, 0-20 g/l of free β-alanine and/or β-alanine salt being supplied to the culture medium, b) passing the D-pantothenate-containing fermentation solution through one or more ion-selective membrane(s) by applying an electric field, low-molecular-weight ions being removed from the D-pantothenate-containing solution, c) adding calcium base and/or magnesium base to set the free D-pantothenic acid contained in the solution to a pH of 5-10, a solution being obtained which contains calcium and/or magnesium pantothenoate and d) subjecting the calcium pantothenate- and/or magnesium pantothenate-containing solution to drying and/or formulation.

In a variant of the inventive process, in step c) or d), a suspension is obtained or charged which contains calcium and/or magnesium pantothenate.

The fermentation taking place in step a) according to the invention can further be carried out using procedures which are known per se in the batch, fed-batch or repeated fed-batch mode or continuously. The resultant pantothenic acid is neutralized in this case using conventional buffer systems, for example phosphate buffer containing NaOH, KOH or ammonia.

In other variants of the inventive process, in step a) at least 10 g/l, preferably at least 20 g/l, particularly preferably at least 40 g/l, very particularly preferably at least 60 g/l, and in particular at least 70 g/l, of salts of D-pantothenic acid are formed in the culture medium by fermentation.

For the purposes of the present invention, the form of words "producing" means that the organism can synthesize larger amounts of D-pentothenic acid and/or salts thereof than are required for its own metabolic needs. In an inventively advantageous variant, the amount of D-pantothenic acid and/or salts thereof synthesized is not present in the interior of the cell, but ideally is completely released into the culture medium by the organism. This discharge can be active or passive by means of mechanisms which are known per se.

According to the invention the D-pantothenic acid-producing organisms used are microorganisms. These include according to the invention fungi, yeasts and/or bacteria. According to the invention, preference is given to using fungi, for example mucor, or yeasts, for example *Saccharomyces* or *Debaromyces*, and of these, preferably, *Saccharomyces cerevisiae*. Advantageously, coryneform bacteria or Bacillaceae are used according to the invention. Those which are within the scope of the invention are preferably, for example, bacteria of the genera *Corynebacterium, Escherichia, Bacillus, Arthrobacter, Bevibacterium, Pseudomonas, Salmonella, Klebsiella, Proteus, Acinetobacter* or *Rhizobium*. Particular preference is given here, for example, to *Corynebacterium glutamicum, Brevibacterium breve* or *Bacillus subtilis, B. licheniformis, B. amyloliquefaciens, B. cereus, B. lentimorbus, B. lentus, B. firmus, B. pantothenticus, B. circulans, B. coagulans, B. megaterium, B. pumilus, B. thuringiensis, B. brevis, B. stearothermophilus* and other *Bacillus*species of group 1 which are characterized by their 16sRNA, or *Actinum mycetalis*. This listing serves for explanation and is in no way limiting for the present invention.

DETAILED DESCRIPTION OF THE INVENTION

Furthermore, the present invention also comprises the use of genetically modified organisms for the inventive preparation of an animal feed supplement containing free D-pantothenic acid and/or salts thereof. Such genetically modified organisms can be isolated, for example, by chemical mutagenesis and subsequent selection using a suitable "screening process". According to the invention, what are termed "production strains" are also included which are suitable for preparing the product in the meaning of the present invention and have genetic modifications with respect to the metabolic flux in the direction of D-pantothenic acid, modifications with respect to the discharge of D-pantothenic acid and/or salts thereof via the cell membrane also being included. This can be achieved, for example, by modifications at key positions in relevant metabolic biosynthesis pathways of the organism used.

It is also conceivable to use transgenic organisms which result from the transfer of homologous and/or heterologous nucleotide sequences which are necessary, or can be required, for synthesizing the desired product. In this case, overexpression and/or deregulation of one or more genes individually and/or in combination localized in the genome and/or on a vector are conceivable.

Transgenic organisms of this type can, advantageously, contain additional copies and/or genetically modified genes selected from the group consisting of panB, panC, panD, panE and/or combinations thereof and/or even organization units how contain the panBCD operon. In addition, other metabolic pathways, for example the isoleucine-valine biosynthesis pathway can be advantageously manipulated in the organisms, as is described, for example, in EP 1 006 189, EP 1 006 192, EP 1 006 193 or EP 1 001 027. As a result, branched-chain precursor substances of pantothenic acid biosynthesis are increasingly being made available. Advantageously, if appropriate, the genes for this biosynthesis pathway, i.e. ilvB, ilvN, ilvC and/or ilvD are overexpressed.

In addition, genetic modifications of aspartate α-decarboxylase (panD), for example through overexpression and/or deregulation, in the D-pantothenic acid-producing organism used are covered by the invention.

The word "deregulation", for the purposes of the present invention, means changing or modifying at least one gene which codes for one enzyme in a biosynthetic metabolic pathway, so that the activity of the enzyme is changed or modified in the microorganism. It is preferred that at least one gene which codes for one enzyme of a biosynthetic metabolic pathway is changed in such a manner that the gene product is formed to an increased extent, or has an increased activity. The term "deregulated metabolic pathway" also includes a biosynthetic metabolic pathway in which more than one gene, which codes more than one enzyme, is changed or modified in such a manner that the activities of more than one enzyme are changed or modified.

Changes or modifications can include, but are not restricted to: removing the endogenous promoter or regulatory elements; introducing strong promoters, inducible promoters or a plurality of promoters simultaneously; removing regulatory sequences, so that expression of the gene product is changed; changing the chromosomal position of the gene; changing the DNA sequence in the vicinity of the gene or within the gene, for example the ribosomal binding site (RBS); increasing the number of copies of the gene in the genome or by introducing a varying number of copies of plasmids; modifying proteins (e.g. regulatory proteins, suppressors, enhancers, transcriptional activators and the like), which play a role in the transcription of the gene and/or in the translation to give the gene product. This also includes all other possibilities for deregulating the expression of genes which belong to the prior art, for example the use of antisense oligonucleotides, or the blocking of repressor proteins.

Deregulation can also comprise changes to the coding region of genes which lead, for example, to removing feedback regulation in the gene product or to a greater or lesser specific activity of the gene product.

Furthermore, genetic modifications to enzymes are advantageous according to the invention which affect the efflux of precursors of pantothenic acid and/or the flux of pantothenic acid to give coenzyme A. Examples of genes coding for such enzymes are: alsD, avtA, ilvE, ansB, coaA, coaX, etc. This listing serves for explanation and is in no way limiting for the present invention.

In addition, genetic modifications are advantageous which secure the cellular production of cofactors (e.g of methylene tetrahydrofolate, redox equivalents and the like) in an amount which is optimum for pantothenic acid production.

Advantageously, thus, β-alanine is already present in the cells in increased concentrations compared with correspondingly non-genetically modified organisms, and thus need not be added to the culture medium as precursor, as is required, for example, in EP-A 0 590 857. Microorganisms are advantageous in which the biosynthesis of pantothenic acid (pan) and/or isoleucine-valine (ilv) and/or asparate-α-decarboxylase (panD) is deregulated. Furthermore, additional overexpression of ketopanthoate reductase (panE) in the microorganisms is advantageous.

It is additionally advantageous according to the invention if, if appropriate, the coaA gene which is required for the synthesis of coenzyme A is decreased in its activity, or is entirely switched off (for example in Bacillus species). This is because Bacillus, in addition to coaA, contains a further gene for this enzymatic function (=coaX). The activity of this gene coaX or the corresponding enzyme can also be changed, preferably reduced, or even deleted, provided that coaA itself still has sufficient enzyme activity, albeit reduced enzyme activity, that is to say the enzyme activity of coaA is not entirely lost. In addition to the overexpression of the various genes, genetic manipulation of the promoter regions of these genes is also advantageous provided that this manipulation leads to overexpression of the gene products.

In an embodiment of the present invention, the bacterial strains described according to the annex (PCT/US application 0025993), for example Bacillus subtilis PA 824 and/or derivatives thereof, are used. In a preferred embodiment, according to the invention the microorganism Bacillus subtilis PA 668, as described in the annex (U.S. Ser. No. 60/262, 995), is used in the inventive process. These strains Bacillus subtilis PA 824 and PA 668 were produced as follows:

Starting from the strain Bacillus subtilis 168 (Marburg strain ATCC 6051), which has the genotype trpC2 (Trp$^-$), the strain PY79 was produced via a transduction of the Trp$^+$ marker (from the Bacillus subtilis wild type W23). Classical genetic engineering methods (as described, for example, in Harwood, C. R. and Cutting, S. M. (editors), Molecular Biological Methods for Bacillus (1990) John Wiley & Sons, Ltd., Chichester, England) introduced mutations ΔpanB and ΔpanE1 into the strain PY79.

The resultant strain was transformed using genomic DNA of Bacillus subtilis strain PA221 (genotype $P_{26}$panBCD, trpC2 (Trp$^-$)) and genomic DNA of Bacillus subtilis strain PA303 (genotype $P_{26}$panE1). The resultant strain PA327 has the genotype $P_{26}$panBCD, $P_{26}$panE1, and is a tryptophan auxotroph (Trp$^-$). Pantothenic acid titers of up to 3.0 g/l (24 h) were achieved using Bacillus subtilis strain PA327 in 10 ml cultures containing SVY medium (25 g/l Difco Veal Infusion Broth, 5 g/l Difco Yeast Extract, 5 g/l of Na glutamate, 2.7 g/l of ammonium sulfate charged into 740 ml of water, the mixture was autoclaved then 200 ml of 1 M potassium phosphate, pH 7.0 and 60 ml of 50% sterile glucose solution were added), which had been supplemented with 5 g/l of β-alanine and 5 g/l of α-ketoisovalerate.

The production of Bacillus subtilis strain PA221 (genotype $P_{26}$panBCD, trpC2 (Trp$^-$)) is described in the following section:

Classic genetic engineering methods were used to clone the panBCD Operon of Bacillus, with the aid of the sequence information of the panBCD Operon of E. coli (see Merkel et al., FEMS Microbiol. Lett., 143, 1996:247-252) starting from a Bacillus subtilis GP275 plasmid library. For the cloning, use was made of E. coli strain BM4062 (bir$^{ts}$) and the information that the Bacillus operon is close to the birA gene. The panBCD operon was introduced into a plasmid which can be replicated in E. coli. To improve the expression of the panBCD operon, strong constitutive promoters of Bacillus subtilis phages SP01 ($P_{26}$) were used, and the ribosome binding site (=RBS) before the panB gene was replaced by an artificial RBS. A DNA fragment which is immediately upstream of the native panB gene in Bacillus was ligated in front of the $P_{26}$panBCD cassette on the plasmid. This plasmid was transformed into Bacillus subtilis strain RL-1 (derivative of Bacillus subtilis 168 obtained by classical mutagenesis (Marburg strain ATCC 6051), genotype trpC2 (Trp$^-$)) and, by homologous recombination, the native panBCD operon was replaced by the $p_{26}$panBCD operon. The resultant strain is called PA221 and has the genotype $P_{26}$panBCD, trpC2 (Trp$^-$).

A pantothenic acid titer of up to 0.92 g/l (24 h) was achieved using the Bacillus subtilis strain PA221 in 10 ml cultures containing SVY medium which had been supplemented with 5 g/l of β-alanine and 5 g/l of α-ketoisovalerate.

Production of the Bacillus subtilis strain PA303 (genotype $P_{26}$panE1) is described in the following section:

Using the E. coli panE gene sequence, the Bacillus panE sequence was cloned by analogy. It was found that in B. subtilis, two homologs of the E. coli panE gene exist which were termed panE1 and panE2. Deletion analyses found that the panE1 gene is responsible for 90% of the pantothenic acid production, while deleting the panE2 gene had no significant effect on pantothenic acid production. Here also, similarly to cloning the panBCD Operon, the promoter was replaced by the strong constitutive promoter $P_{26}$ and the ribosome binding site in front of the panE1 gene was replaced by the artificial binding site. The $P_{26}$panE1 fragment was cloned into a vector which was constructed so that the $P_{26}$panE1 fragment could integrate into the original panE1 locus in the Bacillus subtilis genome. The strain resulting after transformation and homologous recombination is termed PA303 and has the genotype $P_{26}$panE1. A pantothenic acid titer of up to 1.66 g/l (24 h) was achieved using the Bacillus subtilis strain PA303 in 10 ml cultures containing SVY medium which had been supplemented with 5 g/l of β-alanine and 5 g/l of α-ketoisovalerate.

The strain was further constructed by transforming PA327 with a plasmid which contained the $P_{26}$ilvBNC Operon and the marker gene for spectinomycin. The $P_{26}$ilvBNC operon integrated into the amyE locus, which was demonstrated by PCR. One transformant was termed PA340 (genotype $P_{26}$panBCD, $P_{26}$panE1, $P_{26}$ilvBNC, specR, trpC2 (Trp$^-$)).

A pantothenic acid titer of up to 3.6 g/l (24 h) was achieved using the Bacillus subtilis strain PA340 in 10 ml cultures containing SVY medium which had been supplemented only with 5 g/l of β-alanine; in 10 ml cultures containing SVY medium which had been supplemented with 5 g/l of β-alanine and 5 g/l of α-ketoisovalerate, a pantothenic acid titer of up to 4.1 g/l (24 h) was achieved.

In addition, a deregulated ilvD cassette was introduced into strain PA340. For this, a plasmid which contains the ilvD gene under the control of the $P_{26}$ promoter containing the artificial RBS2 was transformed into PA340. The $P_{26}$ilvD gene was integrated into the original ilvD locus by homologous recombination. The resultant strain PA374 has the genotype $P_{26}panBCD$, $P_{26}panE1$, $P_{26}ilvBNC$, $P_{26}ilvD$, specR and trpC2 (Trp⁻).

A pantothenic acid titer of up to 2.99 g/l (24 h) was achieved using the *Bacillus subtilis* strain PA374 in 10 ml cultures containing SVY medium which had been supplemented only with 5 g/l of β-alanine.

In order to produce pantothenic acid using strain PA374 without feed of β-alanine, additional copies of the gene panD coding for aspartate-α-decarboxylase were introduced into strain PA374. For this, chromosomal DNA of strain PA401 was transformed into PA374. Strain PA377 was obtained by selection on tetracycline.

The resultant strain PA377 has the genotype $P_{26}panBCD$, $P_{26}panE1$, $P_{26}ilvBNC$, $P_{26}ilvD$, specR, tetR and trpC2 (Trp⁻).

A pantothenic acid titer of up to 1.31 g/l (24 h) was achieved without feed of precursors using *Bacillus subtilis* strain PA377 in 10 ml cultures containing SVY medium.

Preparation of *Bacillus subtilis* strain PA401 (genotype $P_{26}panD$) is described in the following section:

The *Bacillus subtilis* panD gene was cloned from the pan-BCD operon into a vector which carries the tetracycline marker gene. The promoter $P_{26}$ and an above-described artificial RBS were cloned in front of the panD gene. Restriction digestion produced a fragment which contained the tetracycline marker gene and the $P_{26}panD$ gene. This fragment was religated and transformed into the above-described strain PA221. The fragment integrated into the genome of strain PA211. The resultant strain PA401 has the genotype $P_{26}panBCD$, $P_{26}panD$, tetR and trpC2 (Trp⁻).

A pantothenic acid titer of up to 0.3 g/l (24 h) was achieved using the *Bacillus subtilis* strain PA401 in 10 ml cultures containing SVY medium which had been supplemented with 5 g/l of α-ketoisovalerate. In 10 ml cultures containing SVY medium which had been supplemented with 5 g/l of D-pantoic acid and 10 g/l of L-aspartate, pantothenic acid titers of up to 2.2 g/l (24 h) were achieved.

Starting from strain PA377, a tryptophan-prototrophic strain was generated by transformation with chromosomal DNA from strain PY79. This strain PA824 has the genotype $P_{26}panBCD$, $P_{26}panE1$, $P_{26}ilvBNC$, $P_{26}ilvD$, specR, tetR and Trp⁺.

A pantothenic acid titer of up to 4.9 g/l (48 h) without supply of precursors was achieved using *Bacillus subtilis* strain PA824 in 10 ml cultures in SVY medium (comparison PA377: up to 3.6 g/l in 48 h).

The preparation of PA668 is described in the following section:

The *Bacillus* panB gene was cloned from the wild type panBCD operon and inserted into a vector which, in addition to a chloramphenicol resistance gene, also contains *B. subtilis* sequences of the vpr locus.

The strong constitutive promoter $P_{26}$ was introduced before the 5' end of the panB gene. One fragment which contains the $P_{26}panB$ gene, the marker gene for chloramphenicol resistance and also *Bacillus subtilis* vpr sequences was obtained by restriction digestion. The isolated fragment was religated and used to transform strain PA824. The resultant strain was termed PA668. The genotype of PA668 is: $P_{26}panBCD$, $P_{26}panE1$, $P_{26}ilvBNC$, $P_{26}ilvD$, $P_{26}panB$, specR, tetR, CmR and Trp⁺.

Two colonies of PA668 were isolated and termed PA668-2A, and the other PA668-24.

Using *B. subtilis* strain PA668-2A_ pantothenic acid titers of 1.5 g/l are achieved in 48 h in 10 ml cultures in SVY medium without supply of precursors. In 10 ml cultures supplemented with 10 g/l of aspartate, titers up to 5 g/l are achieved.

Using *B. subtilis* strain PA668-24, pantothenic acid titers of 1.8 g/l are achieved in 48 h in 10 ml cultures in SVY medium without supply of precursors. In 10 ml cultures supplemented with 10 g/l of L-aspartate, titers up to 4.9 g/l are achieved.

The exact construction of the strain is to be taken from the annexes of the PCT/US application 0025993 and U.S. Ser. No. 60/262,995.

Using the above-described strain PA377, in glucose-limited fermentation in SVY medium (25 g/l of Difco Veal Infusion Broth, 5 g/l of Difco Yeast Extract, 5 g/l of tryptophan, 5 g/l of Na glutamate, 2 g/l of $(NH_4)_2SO_4$, 10 g/l of $KH_2PO_4$, 20 g/l of $K_2HPO_4$, 0.1 g/l of $CaCl_2$, 1 g/l $MgSO_4$, 1 g/l of sodium citrate, 0.01 g/l of $FeSO_4.7H_2O$ and 1 ml/l of a trace salt solution of the following composition: 0.15 g of $Na_2MoO_4.2H_2O$, 2.5 g of $H_3BO_3$, 0.7 g of $CoCl_2.6H_2O$, 0.25 g of $CuSO_4.5H_2O$, 1.6 g of $MnCl_2.4H_2O$, 0.3 g of $ZnSO_4.7H_2O$, made up to 1 l with water)) on a 10 l scale with continuous supply of a glucose solution, pantothenic acid concentrations in the fermentation broth of 18-19 g/l 122-25 g/l) are achieved in 36 h (48 h).

In the case of glucose-limited fermentation of PA824, the tryptophan-prototroph derivative of PA377, in yeast extract medium (10 g/l of Difco Yeast Extract, 5 g/l of Na glutamate, 8 g/l of $(NH_4)_2SO_4$, 10 g/l of $KH_2PO_4$, 20 g/l of $K_2HPO_4$, 0.1 g/l of $CaCl_2$, 1 g/l of $MgSO_4$, 1 g/l of sodium citrate, 0.01 g/l of $FeSO_4.7H_2O$ and 1 ml/l of the above-described trace salt solution) the following pantothenic acid concentrations in fermentation broths are achieved in 36 h, 48 h and 72 h: 20 g/l, 28 g/l and 36 g/l, on a 10 l scale with continuous supply of a glucose solution.

By means of further optimization of media, using strain PA824 in glucose-limited fermentation in a medium consisting of 10 g/l of Difco Yeast Extract, 10 g/l of NZ amine A (Quest International GmbH, Erftstadt), 10 g/l of Na glutamate, 4 g/l of $(NH_4)_2SO_4$, 10 g/l of $KH_2PO_4$, 20 g/l of $K_2HPO_4$, 0.1 g/l of $CaCl_2$, 1 g/l of $MgSO_4$, 1 g/l of sodium citrate, 0.01 g/l of $FeSO_4.7H_2O$ and 1 ml/l of the above-described trace salt solution, pantothenic acid concentrations of 37 g/l (48 g/l) are achieved in fermentation broths in 36 h (48 h) on a 10 l scale with continuous supply of a glucose solution.

Further increases in the pantothenic acid concentration in the fermentation broth are conceivable by further optimization of media, by increasing the fermentation time, by process and strain improvement and by combinations of the individual steps. Thus the above-described pantothenic acid concentrations are also achievable by fermentation of strains which are derivatives of the above-described PA824. Derivatives can be prepared by classical strain development and by further genetic engineering manipulations. By development of media, strain and fermentation process, the pantothenic acid titers in the fermentation broths can be increased to greater than 40, 45, 50, 55, 60, 65, 70, 75, 80, 85 and >90 g/l.

An essential advantage of the inventive process is that the fermentation is carried out in a culture medium which, apart from at least one carbon source and nitrogen source, contains no other precursors as starting compounds. That is to say the biosynthesis of D-pantothenic acid is independent of the supply of other precursors. For the purposes of the present invention, such precursors are substances such as β-alanine and/or L-aspartate and/or L-valine and/or α-ketoisovalerate and/or combinations thereof.

In a preferred variant of the inventive process, the fermentation of the D-pantothenic-acid-producing organism is carried out in a culture medium which contains a carbon source and a nitrogen source, but to which no free β-alanine and/or β-alanine salts is/are added or supplied in the course of the fermentation. That is to say for producing D-pantothenic acid in ranges of at least 10 g/l of culture medium, preferably at least 20 g/l, particularly preferably at least 40 g/l, very particularly preferably at least 60 g/l, and in particular at least 70 g/l, no supply of free β-alanine and/or β-alanine salts is required according to the invention.

Independence from feed of precursors is in particular an important economic advantage of the inventive process compared with known processes, since a multiplicity of precursors are very expensive.

However, the invention does not exclude addition of β-alanine and/or β-alanine salts, so that therefore the yield of D-pantothenic acid can be further increased by adding β-alanine and/or β-alanine salts. If it is assumed, for example, that all of the required precursors of pantothenic acid are present in a sufficient amount, only the activity of the panD gene limits a further increase in pantothenic acid production, then the yield of pantothenic acid can be increased, for example, by a further 50% by adding free β-alanine and/or β-alanine salts.

In an advantageous variant of the present invention, up to 20 g/l of free β-alanine and/or β-alanine salts can be added to the culture medium for additional increase in the pantothenic acid yield by more than 50%. Preference is given to adding about 15 g/l of free β-alanine and/or β-alanine salts to the culture medium.

Examples of carbon sources which are suitable according to the invention for use in a culture medium for fermenting the abovementioned organisms are sugars, such as starch hydrolysates (mono-, di-, oligosaccharides), preferably glucose or sucrose, and also beet or cane sugar molasses, proteins, protein hydrolysates, soybean meal, corn steep liquor, fats, free fatty acids, recirculated cells from previous fermentations or hydrolysates thereof, and also yeast extract. This listing is not limiting for the present invention.

In addition, the present process is advantageously distinguished in that the total sugar content is reduced to a minimum up to the end of fermentation, since this would otherwise make difficult later drying and/or formulation of the fermentation solution owing to sticking. This can be achieved according to the invention by continuing the fermentation for some further time after the carbon source is consumed (in the case of batch culture) or after the carbon feed (in the case of a process procedure in the fed-batch or repeated fed-batch mode) is interrupted and/or regulated in such a manner that the concentration of the carbon source is virtually zero (in the case of fed-batch, repeated fed-batch or continuous process procedure).

This is achieved according to the invention by the means that, after interrupting the addition of the carbon source (for example sugar solution), the fermentation is continued until the dissolved oxygen concentration ($pO_2$) of at least 80%, preferably 90%, and particularly preferably 95%, of the saturation value is achieved in the fermentation solution.

Examples of nitrogen sources which are suitable according to the invention are ammonia, ammonium sulfate, urea, proteins, protein hydrolysates or yeast extract. This listing also is not limiting for the present invention.

In addition, the fermentation medium contains mineral salts and/or trace elements, such as amino acids and vitamins. The exact compositions of suitable fermentation media are known in abundance and accessible to those skilled in the art.

After the fermentation medium has been inoculated with a suitable D-pantothenic-acid-producing organism (at the cell densities known to those skilled in the art), if appropriate with addition of an antifoam, the organism is cultured. Any necessary regulation of the pH of the medium can be achieved using various inorganic or organic alkalis or acids, for example NaOH, KOH, ammonia, phosphoric acid, sulfuric acid, hydrochloric acid, formic acid, succinic acid, citric acid or the like.

On account of the buffer systems used during fermentation, which, as described above, can be, for example, NaOH, KOH, ammonia, phosphoric acid, sulfuric acid, hydrochloric acid, formic acid, succinic acid, citric acid or the like, the D-pantothenic acid formed is present in the fermentation solution, depending on the buffer system used, in the form of the respective salt(s). Since in this case according to the invention, in particular, the salts of D-pantothenic acid in the form of their monovalent cations are disadvantageous or D-pantothenic acid in the form of its calcium or magnesium salts are preferred, the fermentation solution is prepared according to the invention via electromembrane separation processes.

The present invention comprises here all available types of electromembrane separation processes, such as membrane electrolyses or electrodialyses. Part of the knowledge of a person skilled in the art is making a suitable choice.

Preference is given according to the invention to the use of electrodialysis. Here, not only electrodialyses using exclusively monopolar membranes can be used, but also electrodialyses using monopolar and/or bipolar membranes. Particular preference is given to electrodialyses using exclusively monopolar membranes, in particular electrodialyses having monopolar membranes which are selective for monovalent ions, called monoselective membranes.

In principle, any membranes customarily used in the context of electrodialysis processes can be used for carrying out the inventive process. The membrane used in the context of the inventive electrodialysis is preferably a commercially conventional ion-exchange membrane.

Anion-exchange membranes which can be used are, for example, Neosepta AM1, AM2, AM3, AMX, AMH, AFN, from Tokuyama Corp., and AMV from Asahi Glass.

Examples of cation-exchange membranes are Neosepta CM1, CM2, CMX, CMH, CMB, Asahi glass CMV, and also Nafion 435 or 350 from Du Pont de Nemours.

A monoselective cation-exchange membrane which may be mentioned is, for example, the membrane Neosepta CMS. Monoselective anion-exchange membranes which can be used are, for example, the membranes Neosepta ACS from Tokuyama Corp. or Selmion ASV from Asahi Glass.

The electrodes used can be stainless steel, nickel, noble metals, for example platinum or other suitable materials known to those skilled in the art.

Using monopolar electrodialysis, according to the invention, not only anions, but also cations can be transferred from the pantothenate-containing solution by migration in the electric field through anion- or cation-exchange membranes into a second solution (concentrate solution, CONC) and thus removed from the pantothenic-acid-containing solution (diluate solution, DIL). Advantageously, according to the invention, low-molecular-weight ions are removed from the pantothenic-acid-containing solution. For the purposes of the present invention, low-molecular-weight ions are those which are introduced into the fermentation broth by the composition of the culture medium and/or the buffer system but are unwanted in the end product. For example, these are the following ions: ammonium, potassium, sodium, iron, chloride, phosphate or sulfate ions.

In a further embodiment of the present invention it is possible to carry out an ion exchange of monovalent cations, such as Na$^+$ or ammonium ions, against polyvalent cations, such as Ca$^{2+}$. For this, cation-exchange membranes which are selective for monovalent ions are used. Thus, for example, in a circuit I a solution of CaCl$_2$ is charged and in a second circuit II separated from circuit I by a cation-exchange membrane the monovalent cation-containing pantothenic acid solution is charged. Then, through a cation-exchange membrane which is selective for monovalent ions and is situated between chamber II and chamber III, preferably monovalent cations are transferred into a third chamber III. At the same time, anions, such as chloride ions, are transferred from chamber I into chamber III through an anion-exchange membrane situated between chamber I and chamber III. Ca$^{2+}$ ions are transferred from chamber I into chamber II through a cation-exchange membrane. In this manner calcium D-pantothenate is obtained directly. When a salt of a weak acid, for example pantothenic acid, is present, free D-pantothenic acid may also be produced in such an arrangement if, instead of CaCl$_2$, an aqueous HCl solution is charged into chamber I.

The invention also comprises the use of calcium salts and/or magnesium salts in the form of inorganic or organic anions. Advantageously, according to the invention, calcium and/or magnesium chloride, nitrate, hydroxide, formate, acetate, propionate, glycinate or lactate are used.

In an alternative embodiment of the present invention, when bipolar electrodialysis is used, advantageously, cations can be transferred into a second solution from the pantothenate-containing solution through cation-exchange membranes and thus removed from the pantothenic-acid-containing solution, with simultaneous provision of protons, by dissociation of water in the bipolar membrane. In the second solution, the corresponding bases of the cations which have been transferred are formed using hydroxide ions provided by dissociation of water in the bipolar membrane.

In another embodiment of the present invention, when bipolar electrodialysis is used, advantageously, anions can be transferred into a second solution from the pantothenate-containing solution through an anion-exchange membrane and thus removed from the pantothenic-acid-containing solution, with simultaneous provision of hydroxide ions, by dissociation of water in the bipolar membrane. In the second solution, the corresponding acids of the anions which have been transferred are formed using protons provided by dissociation of water in the bipolar membrane.

The invention also comprises a further alternative embodiment in which, by using bipolar electrodialysis, firstly, advantageously, anions are transferred from the pantothenate-containing solution into a second solution through anion-exchange membranes and thus removed from the pantothenic acid-containing solution, with simultaneous provision of hydroxide ions, by dissociation of water in the bipolar membrane, and secondly cations are transferred from the pantothenate-containing solution into a third solution through cation-exchange membranes and thus removed from the pantothenic-acid-containing solution, with simultaneous provision of protons, by dissociation of water in the bipolar membrane. In the second solution, the corresponding acids of the anions transferred reformed using the protons provided by dissociation of water in the bipolar membrane, and in the third solution, the corresponding bases of the cations transferred are formed using hydroxide ions provided by dissociation of water in the bipolar membrane.

Preferably, according to the invention, in the present process, moreover, the pH of the pantothenate-containing solution is set to the isoelectric point of pantothenic acid using acids or bases. Owing to this, the yield of free D-pantothenic acid can be further increased or the loss can be further minimized.

The monopolar electrodialysis is a particularly preferred variant, since it is highly cost-effective compared with bipolar electrodialysis.

Bipolar electrodialysis may be used, in particular, when acids or bases are not to be added to adjust the pH, or the existing acid or alkali metal hydroxide solution can be further used.

All electrodialysis variants, according to the invention, offer the advantage that no wastewater is produced from the regeneration of ion-exchange resins.

The inventive use of the electroseparation processes preferably removes the unwanted low-molecular-weight ions (foreign ions), such as ammonium, potassium, sodium, iron, chloride, phosphate or sulfate ions, from the D-pantothenate-containing solution. That is to say, preferably, free D-pantothenic acid or the desired salts are formed, such as calcium and/or magnesium D-pantothenate.

According to the invention, the content of monovalent cations, preferably ammonium, potassium and/or sodium ions, is decreased to a concentration of $\leq 1$ g/kg of solution.

The content of unwanted anions, for example chloride, sulfate or phosphate ions, can also be significantly decreased by the choice of ion-exchange membrane, preferably by using an anion-exchange membrane.

The resultant solution containing free D-pantothenic acid is according to the invention set to a pH of 3-10 by adding calcium base and/or magnesium base. A pH of 5-10 is advantageous. Preferably, the pH is set to a value of 5-9, particularly preferably 6-9, and very particularly preferably 6-8. In this manner a solution containing calcium pantothenate and/or magnesium pantothenate is obtained. Preferably, for neutralization, calcium hydroxide, calcium carbonate, calcium oxide, magnesium hydroxide and/or basic magnesium carbonate is added to the solution in the form of a solid and/or as aqueous suspension.

It is preferred according to the invention in this case if the free D-pantothenic-acid-containing solution is neutralized with a calcium base and/or magnesium base in the form of an aqueous suspension. As a result of using an aqueous dispersion the neutralization is performed more rapidly and without relatively large pH fluctuations than is the case when a corresponding solid is used.

According to the invention the process is distinguished in that an aqueous suspension comprising 2-55% by weight, preferably 10-50% by weight, and particularly preferably 20-40% by weight, of calcium hydroxide is added to the solution in step c). The invention additionally comprises a process in which an aqueous suspension comprising 2-65% by weight, preferably 10-50% by weight, and particularly preferably 20-40% by weight, of calcium carbonate is added to the solution in step c). In a further embodiment of the present invention, an aqueous suspension comprising 2-60% by weight, preferably 10-50% by weight, and particularly preferably 20-40% by weight, of magnesium hydroxide is added to the solution in step c) of the inventive process. The invention also comprises a process in which an aqueous suspension comprising 2-25% by weight, preferably 10-20% by weight, of basic magnesium carbonate is added to the solution in step c).

The fermentation solution is dried and/or formulated using processes known per se, for example spray drying, spray granulation, fluidized-bed drying, fluidized-bed granulation, drum drying or spin-flash drying (Ullmann's Encyclopedia of Industrial Chemistry, 6$^{th}$ edition, 1999, electronic release, chapter "Drying of Solid Materials"). The gas inlet temperature in convection drying is in the range 100-280° C., preferably 120-210° C. The gas outlet temperature is 50-180° C., preferably 60-150° C. To establish a desired particle size distribution and the associated product properties, fine particles can be separated off and recirculated. In addition, coarse material can be ground in a mill and likewise then recirculated.

According to the invention, in the process described above, the reduction of complex workup steps is advantageous, in particular the avoidance of the use of organic solvents, with simultaneous production of a desired product having high biological value. In addition, according to the invention the amount of waste water produced is significantly reduced. This thus results in further savings in complex work up and disposal plants. Thus the inventive process is advantageously distinguished in that it is simpler, less susceptible to faults, less time-consuming, markedly less expensive and thus more economical than conventional processes.

However, this does not exclude the inventive process from being able to be varied. The inventive process steps a) to d) mentioned at the outset can be supplemented by one or more of the following process steps which are themselves familiar to those skilled in the art. In this case, all conceivable combinations of the additional (operational) process steps with the (essential) process steps a) to d) are covered by the invention.

Thus the solutions resulting from the process steps a)-c) can be disinfected, for example by heating (sterilization) or other methods, for example pasteurization or sterile filtration.

In other variants of the inventive process, before the drying and/or formulation of the solution, at least one of and/or combinations of the following steps can be carried out, comprising lysis and/or sterilizing the biomass and/or separating off the biomass from the fermentation solution and/or adding further additives and/or concentrating the fermentation solution, preferably by removing water.

The present invention thus also relates to a process in which the lysis and/or sterilization of the biomass is carried out still in the fermentation solution or not until after the biomass is separated off from the fermentation solution. This can be performed, for example, by a temperature treatment, preferably at 80-200° C., and/or an acid treatment, preferably with sulfuric acid or hydrochloric acid, and/or enzymatically, preferably with lysozyme.

In a further embodiment of the present invention, the cells of the fermented microorganisms can be removed by filtration, separation (for example centrifugation) and/or decantation from the solutions of the steps a), b) or c) of the inventive process. It is also conceivable for the solutions of the steps a), b) or c), without separating off the organisms present, to be passed directly through one or more ion-selective membrane (s) by applying an electric field.

The solution resulting from the work up via membrane electrolysis or electrodialysis can, following neutralization, be concentrated via a suitable evaporator, for example falling-film evaporator, thin-film evaporator or rotary evaporator. Such evaporators are manufactured, for example, by the companies GIG (4800 Attnang Puchheim, Austria), GEA Canzier (52303 Duren, Germany), Diessel (31103 Hildesheim, Germany) and Pitton (35274 Kirchhain, Germany).

To improve the color properties of the end product, an additional filtration step can be carried out in which a little activated carbon is added to the solutions obtained during the process and this suspension is then filtered. Or, the solutions obtained during the fermentation can be passed through a small activated carbon bed. The amounts of activated carbon used which are required for this are in the range of a few % by weight of the solution and are within the knowledge and experience of those skilled in the art.

These filtrations can be simplified by adding a commercial flocculating aid to the respective solution before filtration (for example Sedipur CF 902 or Sedipur CL 930 from BASF AG, Ludwigshafen).

In an advantageous embodiment of the present invention, the fermentation output (fermentation broth) is sterilized by heating and is then freed from the cell mass by centrifugation, filtration or decantation. After addition of 50-1000 mg/kg, preferably 100-200 mg/kg, of a commercially conventional flocculating aid, based on the fermentation output, the mixture is filtered through a short bed of activated carbon and sand in order to obtain a biomass-free solution having a high D-pantothenic acid content. This treated solution is then passed through one or more ion-selective membrane(s) by applying an electric field.

This solution can then be dried, for example by spray drying. This can be performed in cocurrent, countercurrent or mixed flow. For the atomization, all known atomizers can be used, in particular centrifugal atomizers (atomizer disk), single-fluid nozzle or two-fluid nozzle. Preferred drying temperature conditions are 150-250° C. tower inlet temperature and 70-130° C. tower exit temperature. However, drying can also be performed at higher or lower temperature levels. To achieve a very low residual moisture, a further drying step can be provided downstream in a fluidized bed.

The spray drying may also be carried out in an FSD or SBD dryer (FSD: fluidized spray dryer; SBD: spray bed dryer), as are manufactured by the companies Niro (Copenhagen, Denmark) and APV-Anhydro (Copenhagen, Denmark), which are a combination of spray dryer and fluidized bed.

In the spray drying an anticaking agent can be added. This can reduce the deposition on the dryer wall and improve the flow behavior, precisely in the case of fine-grained powders. Anticaking agents which can be used are, in particular, silicates, stearates, phosphates and corn starch.

In principle the drying can also take place in a sprayed fluidized bed, in which case this can be operated not only continuously but also batchwise. The solution can be sprayed in not only from the top (top spray) and from the bottom (bottom spray) but also from the side (side spray).

The present invention further relates to a composition for use as animal feed additive and/or animal feed supplement, in which case it can be prepared by a) using at least one organism which produces D-pantothenic acid and in which the biosynthesis of pantothenic acid (pan) and/or isoleucine/valine (ilv) is deregulated and which forms at least 2 g/l of salts of D-pantothenic acid by fermentation in a culture medium, 0-20 g/l, preferably 0 g/l, of free β-alanine and/or β-alanine salt being supplied to the culture medium, b) passing the D-pantothenate-containing fermentation solution through one or more ion-selective membrane(s) by applying an electric field, low-molecular-weight ions being removed from the D-pantothenate-containing solution, c) adding a calcium base and/or magnesium base to set the free D-pantothenic acid contained in the solution to a pH of 3-10, a solution being obtained which contains calcium and/or magnesium pantothenate acid and d) subjecting the calcium pantothenate- and/or magnesium pantothenate-containing solution to drying and/or formulation.

In a variant of the present invention, the composition is distinguished in that, in step c) or d), a suspension is obtained or charged which comprises calcium pantothenate and/or magnesium pantothenate.

According to the invention the composition is further distinguished in that it comprises salts of D-pantothenic acid at a concentration of at least 1-100% by weight, preferably at least 20-100% by weight, and particularly preferably at least 50% by weight. The present invention relates to a composition which comprises salts of D-pantothenic acid in the form of divalent cations, preferably calcium and/or magnesium D-pantothenate. According to the invention preference is given to a composition which is distinguished in that the content of salts of D-pantothenic acid in the form of monovalent cations is $\leq 1$ g/kg.

According to the invention by means of the above-described process a calcium D-pantothenate or magnesium D-pantothenate is obtained which meets the requirements for a feed additive. These requirements are, for example, a relatively high content of D-pantothenate and a high compatibility with the target organism and biological value in the meaning of "vitamin activity" of the inventive product.

The present invention will be described in more detail by the following examples, which are not, however, limiting for the invention:

EXAMPLE 1

In a laboratory fermenter containing stirrer and gas-introduction device of 14 l capacity, aqueous fermentation medium of the following composition was charged:

| Starting material | Concentration [g/l] |
| --- | --- |
| Yeast extract | 10 |
| Sodium glutamate | 5 |
| Ammonium sulfate | 8 |
| Antifoam | 1 ml/l |

After sterilization, the following sterile media components were additionally added:

| Starting material | Concentration [g/l] |
| --- | --- |
| $KH_2PO_4$ | 10 |
| $K_2HPO_4$ | 20 |
| Glucose | 2.5 |
| Calcium chloride | 0.1 |
| Magnesium chloride | 1 |
| Sodium citrate | 0.1 |
| $FeSO_4 \times 7H_2O$ | 0.1 |
| Trace salt solution | 1 ml/l |

The trace salt solution has the following composition:

0.15 g of $Na_2MoO_4.2H_2O$, 2.5 g of $H_3BO_3$, 0.7 g of $COCl_2.6H_2O$, 0.25 g of $CuSO_4.5H_2O$, 1.6 g of $MnCl_2.4H_2O$, 0.3 g of $ZnSO_4.7H_2O$ are made up to 1 l with water. The trace salt solution is added via sterile filtration. The initial liquid volume is 8.4 l. The contents set forth above are based on this value.

To this solution are added 160 ml of inoculation culture (OD=10 in SVY medium (SVY medium: Difco Veal Infusion broth 25 g, Difco Yeast Extract 5 g, sodium glutamate 5 g, 2.7 g of $(NH_4)_2SO_4$ in 740 ml of $H_2O$, sterilize; add 200 ml of sterile 1M $K_2HPO_4$ (pH 7) and 60 ml of sterile 50% glucose solution (final volume 1 L))) of *Bacillus subtilis* PA824 and it is fermented at 43° C. with vigorous stirring at a gas flow rate of 12 l/min. This strain is described in accordance with the annex in PCT/US Application 0025993.

Within the course of 52 h, 6 l of a sterile aqueous solution were added. The composition was:

| Starting material | Concentration [g/l] |
| --- | --- |
| Glucose | 500 |
| Calcium chloride | 0.6 |
| Trace salt solution | 7 ml/l |

The fermentation was carried out under glucose-limiting conditions. During the fermentation the pH was kept at 7.2 by adding 25% strength ammonia solution or 20% strength phosphoric acid. Ammonia serves simultaneously as nitrogen source for the fermentation. The speed of rotation of the agitator element was controlled to keep the dissolved oxygen content to 30% of the saturation value. Foaming was controlled by occasional addition of an antifoam. After halting the addition of the carbon source, the fermentation was continued until the dissolved oxygen content ($pO_2$) had reached a value of 95% of the saturation value. The fermentation was then ended and the organism was thermally destroyed. For this the fermentation solution was sterilized for 60 min. Destruction was demonstrated by plating out. The cells are then separated off by centrifugation. After cell separation the concentration of D-pantothenate after 52 h is 24.7 g/l.

Similarly, fermentation broths may also be produced which have β-alanine-feed-free pantothenic acid titers of greater than 20, 25, 30, 35, 40, 45, 50, 55, 60, 65, 70, 75, 80, 85 and >90 g/l.

The fermentation output which is sterilized by heating as described above and has been substantially freed from the biomass by centrifugation was admixed with additional D-pantothenic acid and the pH was set to approximately 2 with sulfuric acid. The resultant solution was filtered through a small bed of sand/activated carbon. The content of D-pantothenic acid in this solution is 67.7 g/l.

900 g of this filtrate were treated by electrodialysis as follows: in an electrodialysis cell (fitted with anion- and cation-exchange membranes (types Neosepta AMX Sb and CMX Sb, respectively, from Tokuyama Corp.) having an effective cell area of 1.85 $dm^2$ and five chambers, the filtrate was desalted at an initial current density of 29 $mA/cm^2$. The current density decreased continuously in an experimental run after reaching the preset limit voltage of 20 V. The temperature was from 33° C. to 40° C. As concentrate feed, 0.5% strength (w/w) NaCl solution was charged. This concentrate (CONC) was enriched in an experimental run with the foreign ions (e.g. ammonium, chloride, iron, potassium, sodium or phosphate ions) removed from the filtrate (diluate, DIL). In the electrolyte cycle, to flush the electrodes 5% strength (w/w) sodium sulfate solution was charged. In the experimental run, at various ionic conductivity values of the diluate solution, samples were taken from the diluate-containing chamber and analyzed. The analysis is presented in the following table and showed that with advancing experiment time, said ions had been removed from the diluate and the conductivity of the diluate decreases correspondingly. Small monovalent ions, for example chloride ions, are removed more rapidly than high-volume multivalent ions, for example phosphate ions.

The results of the analysis of the diluate may be taken from the table below.

| | | Ions (U laboratory analysis) | | | | | | | |
|---|---|---|---|---|---|---|---|---|---|
| | PTA g/l | Ammonium | Cl | o-Phosphate | Ca | Fe | K | Mg | Na |
| Starting material (mS/cm) | 67.7 | 0.35-0.40% | 0.90-0.97% | 0.61-0.79% | 0.009% | <0.001% | 0.45% | 0.002% | — |
| 4831/00/196 DIL 25 mS/cm | 67.9 | 0.22% | 0.65% | 0.56% | 0.005% | <0.001% | 0.30% | 0.002% | 0.089% |
| 4831/00/196 DIL 20 mS/cm | 70.7 | 0.16% | 0.49% | 0.53% | 0.004% | <0.001% | 0.23% | 0.002% | 0.077% |
| 4831/00/196 DIL 15 mS/cm | 64.1 | 0.12% | 0.32% | 0.54% | 0.003% | <0.001% | 0.16% | 0.001% | 0.063% |
| 4831/00/196 DIL 10 mS/cm | 73.2 | 0.08% | 0.16% | 0.48% | 0.002% | <0.001% | 0.099% | 0.001% | 0.047% |
| 4831/00/196 DIL 5 mS/cm | 79.9 | 0.03% | 0.04% | 0.35% | 0.001% | <0.001% | 0.038% | 0.001% | 0.025% |
| 4831/00/196 DIL 3 mS/cm | 75.6 | 0.02% | 0.01% | 0.26% | 0.001% | <0.001% | 0.016% | <0.001% | 0.015% |
| 4831/00/196 DIL-end | 76.0 | 0.01% | <0.01% | 0.21% | <0.001% | <0.001% | 0.009% | <0.001% | 0.010% |

PTA = pantothenic acid

The pHs of all diluate samples was 2-3. 771 g of the diluate discharge contains 76 g/l of free D-pantothenic acid.

It is shown here that a D-pantothenic acid solution obtained by fermentation can be successfully freed from interfering cations by electrolysis. A non-hygroscopic calcium D-pantothenate powder, as described in example 2, may be prepared from the desalted D-pantothenic acid which is obtained.

EXAMPLE 2

In a laboratory fermenter containing stirrer and gas-introduction device of 14 l capacity, aqueous fermentation medium of the following composition was charged:

| Starting material | Concentration [g/l] |
|---|---|
| Yeast extract | 10 |
| Sodium glutamate | 5 |
| Ammonium sulfate | 8 |
| $KH_2PO_4$ | 8.4 |
| $K_2HPO_4$ | 15 |

After sterilization, the following sterile media components were additionally added:

| Starting material | Concentration [g/l] |
|---|---|
| Glucose | 2.5 |
| Calcium chloride | 0.1 |
| Magnesium chloride | 1 |
| Sodium citrate | 1 |
| $FeSO_4.7H_2O$ | 0.01 |
| Trace salt solution | 1 ml |

The trace salt solution has the following composition: 0.15 g of $Na_2MoO_4.2H_2O$, 2.5 g of $H_3BO_3$, 0.7 g of $CoCl_2.6H_2O$, 0.25 g of $CuSO_4.5H_2O$, 1.6 g of $MnCl_2.4H_2O$, 0.3 g of $ZnSO_4.7H_2O$ are made up to 1 l with water. The trace salt solution is added via sterile filtration. The initial liquid volume is 5.5 l. The contents set forth above are based on this value.

To this solution are added 55 ml of inoculation culture (OD=10 in SVY medium (SVY medium: Difco Veal Infusion broth 25 g, Difco Yeast extract 5 g, sodium glutamate 5 g, dissolve 2.7 g of $(NH_4)_2SO_4$ in 740 ml of $H_2O$, sterilize; add 200 ml of sterile 1M $K_2HPO_4$ (pH 7) and 60 ml of sterile 50% glucose solution (final volume 1 L))) of *Bacillus subtilis* PA824 and it is fermented at 43° C. under vigorous stirring at a gas flow rate of 12 l/min. This strain is described in accordance with the annex in PCT/US Application 0025993.

Within the course of 48 h, 6 l of a sterile aqueous solution were added. The composition was:

| Starting material | Concentration [g/l] |
|---|---|
| Glucose | 550 |
| Calcium chloride | 0.6 |
| Trace salt solution | 6 ml |

The fermentation was carried out under glucose-limiting conditions. During the fermentation the pH was kept at 7.2 by adding 25% strength ammonia solution or 20% strength phosphoric acid. Ammonia serves simultaneously as nitrogen source for the fermentation. The speed of rotation of the agitator element was controlled to keep the dissolved oxygen content to 30% of the saturation value. Foaming was controlled by occasional addition of an antifoam. After halting the addition of the carbon source, the fermentation was continued until the dissolved oxygen content ($pO_2$) had reached a value of 95% of the saturation value. The fermentation was then ended and the organism was thermally destroyed. For this the fermentation solution was sterilized for 30 min. Destruction was demonstrated by plating out. The cells were separated off by centrifugation. After cell separation the concentration of D-pantothenate after 48 h was 24.1 g/l.

Similarly, fermentation broths may also be produced which have β-alanine-feed-free pantothenic acid titers of greater than 20, 25, 30, 35, 40, 45, 50, 55, 60, 65, 70, 75, 80, 85 and >90 g/l.

2 817 ml of the fermenter output were admixed with 1 183 ml of a pantothenic acid solution of concentration 178.9 g/l and neutralized with 25% strength ammonium hydroxide solution (pH 6.5). The mixture is then filtered through sand/activated carbon. The content of D-pantothenic acid in the filtrate was 67 g/l, principally in the form of the ammonium salt. Approximately 720 g of this solution were treated by electrodialysis according to example 1:

550 g of the diluate discharge (having a density of 1.017 g/ml) were adjusted to a pH of 7.5 using 3.5 g of a 40% strength calcium hydroxide suspension. An aqueous calcium D-pantothenate solution was obtained (551.03 g having a calcium D-pantothenate content of 40.9 g/l). The aqueous calcium pantothenate solution was dried in a Niro Minor laboratory spray dryer. The tower inlet temperature was about 200° C. and the tower outlet temperature was 90° C. Atomization was performed by means of a two-fluid nozzle at a pressure of 2 bar. The powdering agent added was Sipernat 22F. A pulverulent product of the following specification was obtained (figures in % by weight):

Water content: 2.3%
Calcium D-pantothenate: 46.1%
Ammonium: 0.60%
Potassium: 0.47%
Sodium: 1.1%

EXAMPLE 3

In a fermenter containing agitator and gas-introduction device of 200 liters capacity, 800 g of 50% strength yeast extract, 438 g of Na glutamate, 3200 g of soybean flour, 640 g of ammonium sulfate, 800 g of $KH_2PO_4$, 1 600 g of $K_2HPO_4$ and 50 ml of antifoam TegoKS were admixed with 70 l of water and the mixture was sterilized for 30 min at 121° C.

Solution 1 and solution 2 were then added.

Solution 1 was made up as follows: 1670 g of glucose.$H_2O$, 10.2 g of $CaCl_2.2H_2O$ and 170.7 g of $MgCl_2.6H_2O$ are dissolved in 9 l of water and sterilized for 30 min.

Solution 2 is made up as follows: 800 ml of citrate-iron solution (200 g/l of sodium citrate, 2 g/l of $FeSO_4.7H_2O$, sterile-filtered) are admixed with 80 ml of trace salt solution (0.15 g of $Na_2MoO_4.2H_2O$, 2.5 g of $H_3BO_3$, 0.7 g of $CoCl_2.6H_2O$, 0.25 g of $CuSO_4.5H_2O$, 1.6 g of $MnCl_2.4H_2O$, 0.3 g of $ZnSO_4.7H_2O$ are made up to 1 l with water, and sterile-filtered).

To this solution were added 2 l of inoculation culture (OD=10 in SVY medium (SVY medium: Difco Veal Infusion broth 25 g, Difco Yeast extract 5 g, sodium glutamate 5 g, 2.7 g of $(NH_4)_2SO_4$ in 740 ml of $H_2O$, sterilize; add 200 ml of sterile 1M $K_2HPO_4$ (pH 7) and 60 ml of sterile 50% glucose solution (final volume 1 l))) of *Bacillus subtilis* PA668 and it was fermented at 43° C. with vigorous stirring at a gas flow rate of 3 $m^3$/min. This strain is described in accordance with the annex in U.S. Ser. No. 60/262,995.

In the course of 48 h, approximately 10 l of a sterile aqueous glucose solution were added. The solution was made up as follows: 90 kg of glucose.$H_2O$ were admixed with 55 kg of water and sterilized for 30 min. Then 300 ml of trace salt solution (see above for composition) and 3 l of citrate-iron solution (see above for composition) were added. Then, 1 l of sterile-filtered 90 g/l $CaCl_2.2H_2O$ solution and 2 l of sterile-filtered 375 g/l of sodium glutamate solution were added.

The fermentation was carried out under glucose-limiting conditions. During the fermentation the pH was kept at 7.2 by adding 25% strength ammonia solution or 20% strength phosphoric acid. Ammonia serves simultaneously as nitrogen source for the fermentation. The speed of rotation of the agitator element was controlled to keep the dissolved oxygen content to 30% of the saturation value. Foaming was controlled by occasional addition of an antifoam. After halting the addition of the carbon source, the fermentation was continued until the dissolved oxygen content ($pO_2$) had reached a value of 95% of the saturation value. The fermentation was then ended. The cells were separated off by separation in a disk separator. Remaining cells in the supernatant were thermally destroyed by sterilization. The concentration of D-pantothenate at stopping after 48 h was 13.7 g/l. After separation and sterilization the concentration of D-pantothenate was 10.7 g/l. Similarly, fermentation broths can also be produced which have β-alanine-feed-free pantothenic acid titers of greater than 15, 20, 25, 30, 35, 40, 45, 50, 55, 60, 65, 70, 75, 80, 85, and greater than 90 g/l.

3 000 g of the fermentation solution thus pretreated were further processed as follows: two thirds of the batch were precipitated at approximately 10° C. with an amount of $CaCl_2$ corresponding to the equivalent concentration of multivalent anions (40% solution); one third of the batch was correspondingly precipitated with an equivalent amount of $Ca(OH)_2$ (solid). The solutions were stored in a refrigerator overnight and then separated from the precipitated sediment by means of a pressure filter (Seitz depth filter 700). The solutions were then mixed and made basic (pH=8.7) by adding a further 10 g of $Ca(OH)_2$ at approximately 10° C. and reprecipitated. The reprecipitated sediment was likewise filtered off.

1 800 g of the solution were then salt-exchanged at 35° C. in a three-circuit electrodialysis stack. In this case the fermentation broth was passed through a product chamber bounded by two cation exchange membranes. On the cathode side a monoselective cation-exchange membrane (Tokuyama Soda, CMS) separated the product from the concentrate circuit, and on the anode side the product chamber was separated from the $CaCl_2$ circuit by a conventional cation-exchange membrane (Tokuyama Soda, CMX). Concentrate and $CaCl_2$ circuit were separated by an anion-exchange membrane (Tokuyama Soda, AMX). In the concentrate, 750 g of a 0.5% strength NaCl solution were charged, and in the $CaCl_2$ circuit 900 g of a 3.05% strength $CaCl_2$ solution were charged. In the electrode-flushing circuit, a 0.1 molar $Na_2SO_4$ solution was circulated. The experiment was carried out galvanostatically at 30 $mA/cm^2$ in a stack consisting of five of the basic units described above having a total membrane area of 500 $cm^2$ in batch mode. The criterion chosen for stopping was a minimum conductivity of 4 mS/cm in the $CaCl_2$ circuit. The results of cation analysis in the product and concentrate circuits are summarized in the table below.

|  | PTA [g/l] | $Ca^{2+}$ | $Na^+$ | $K^+$ | $NH_4+$ |
| --- | --- | --- | --- | --- | --- |
| 5329/01/82 Product t = 0 | 9.27 | 0.24% | 0.15% | 0.65% | 0.24% |
| 5329/01/82 Product t = 0.83 h | 9.01 | 0.43% | 0.07% | 0.25% | 0.06% |
| 5329/01/82 Concentrate t = 0 h | 0.0 | 0.0% | 0.2% | 0.0% | 0.0% |
| 5329/01/82 Concentrate t = 0.83 h | 0.015 | 0.02% | 0.47% | 0.71% | 0.29% |

From this are calculated depletions of 51% for sodium, 66% for ammonium and 61% for potassium. The mean current yield was 82%. The loss of pantothenic acid in the two adjoining circuits was in each case 0.08% of the amount of substance used. The pH of the product circuit was 7-7.5 during the experiment, and in the concentrate and $CaCl_2$ circuit was approximately pH=6. The total voltage drop increased in the course of the experiment in accordance with the decreasing conductivity in the $CaCl_2$ circuit from approximately 11 to 16 V.

The solution thus treated by electrodialysis was then successfully spray-dried to give the end product. It is shown here that in the event of appropriate pretreatment a three-circuit electrodialysis using a monoselective cation-exchange membrane can be used for the ion exchange of monovalent cations against divalent cations to increase the ability of the end product to be spray-dried.

We claim:

1. A process for preparing D-pantothenic acid and/or salts thereof which comprises
   a) culturing at least one bacterium from the Bacillaceae family which produces D-pantothenic acid and in which the biosynthesis of pantothenic acid (pan) and/or isoleucine/valine (ilv) is deregulated and which forms at least 2 g/L of salts of D-pantothenic acid by fermentation in a culture medium,
   b) passing the D-pantothenate-containing fermentation solution through at least one ion-selective membrane by applying an electric field, wherein the concentration of monovalent ions selected from the group consisting of ammonium, potassium, sodium and chloride, and/or polyvalent ions selected from the group consisting of iron, phosphate and/or sulfate ions is reduced in the D-pantothenate-containing solution,
   c) adding a calcium base and/or magnesium base to the resulting solution containing free D-pantothenic acid to set the pH to between 3-10, a solution being obtained which contains calcium and/or magnesium pantothenate and
   d) subjecting the calcium pantothenate- and/or magnesium pantothenate-containing solution to drying and/or formulation wherein no free β-alanine and/or β-alanine salt is fed to the culture medium.

2. A process as claimed in claim 1, wherein the bacterium is of the genus *Bacillus*.

3. A process as claimed in claim 1, wherein, in step a) a content of D-pantothenic acid and/or salts thereof of at least 10 g/l of culture medium is formed.

4. A process as claimed in claim 1, wherein, in step c), the pH of the solution is set to 5-10.

5. A process as claimed in claim 1, wherein, in step c), the pH of the solution is set to 5-9.

6. A process as claimed in claim 1, wherein, in step b), monopolar and/or bipolar ion-exchange membranes are used.

7. A process as claimed in claim 1, wherein, in step b), monopolar ion-exchange membranes are used.

8. A process as claimed in claim 1, wherein, in step b), monoselective ion-exchange membranes are used.

9. A process as claimed in claim 1, wherein the pH of the D-pantothenic-acid-containing fermentation solution, before the treatment in step b), is set to the isoelectric pH of D-pantothenic acid.

10. A process as claimed in claim 1, wherein, in step b), monopolar and/or bipolar ion-exchange membranes are used and current densities of 1-100 $mA/cm^2$ are set for the monopolar ion-exchange membranes.

11. A process as claimed in claim 1, wherein, in step b), monopolar and/or bipolar ion-exchange membranes are used and current densities of 1-150 $mA/cm^2$ are set for the bipolar ion-exchange membranes.

12. A process as claimed in claim 1, wherein in step b), the concentration of monovalent cations is reduced to a concentration of ≦1 g/kg of solution.

13. A process as claimed in claim 1, wherein, for neutralization, calcium hydroxide, calcium carbonate, calcium oxide, magnesium hydroxide and/or basic magnesium carbonate is added in the form of a solid and/or as aqueous suspension to the solution in step c).

14. A process as claimed in claim 1, wherein an aqueous suspension comprising 2-55% by weight of calcium hydroxide is added to the solution in step c).

15. A process as claimed in claim 1, wherein an aqueous suspension comprising 2-65% by weight of calcium carbonate is added to the solution in step c).

16. A process as claimed in claim 1, wherein an aqueous suspension comprising 2-60% by weight of magnesium hydroxide is added to the solution in step c).

17. A process as claimed in claim 1, wherein an aqueous suspension comprising 2-25% by weight of basic magnesium carbonate is added to the solution in step c).

18. A process as claimed in claim 1, wherein, in step c) a suspension is obtained which contains calcium pantothenate and/or magnesium pantothenate.

19. A process as claimed in claim 1, wherein the bacterium is genetically modified such that cells of the bacterium contain β-alanine in increased concentrations compared with a corresponding non-genetically modified bacterium.

20. A process as claimed in claim 1, wherein, in step a) a content of D-pantothenic acid and/or salts thereof of at least 40 g/l of culture medium is formed.

* * * * *